United States Patent [19]

Miller et al.

[11] 4,315,838

[45] Feb. 16, 1982

[54] CATALYST PREPARATION TECHNIQUE

[75] Inventors: Arthur F. Miller, Lyndhurst; James L. Callahan, Wooster; Wilfrid G. Shaw, Lyndhurst, all of Ohio

[73] Assignee: Standard Oil Company, Cleveland, Ohio

[21] Appl. No.: 912,651

[22] Filed: Jun. 5, 1978

[51] Int. Cl.$^3$ .............................................. B01J 37/00
[52] U.S. Cl. .................................. 252/448; 252/437; 252/454; 252/461
[58] Field of Search ................ 252/437, 448, 454, 461

[56] References Cited

U.S. PATENT DOCUMENTS 3,642,930 2/1972 Grasselli et al. ................ 252/456 X
3,966,639 6/1976 Callahan et al. ..................... 252/439

*Primary Examiner*—W. J. Shine
*Attorney, Agent, or Firm*—John E. Miller, Jr.; Herbert D. Knudsen; Larry W. Evans

[57] ABSTRACT

Catalysts with improved catalytic properties are produced by a novel process in which not all of the heat-decomposable salt in the pre-catalyst is driven off during pre-heating and the powdery pre-catalyst obtained by pre-heating is agglomerated by dropping a slurry of the powder onto a particle bed.

11 Claims, No Drawings

CATALYST PREPARATION TECHNIQUE

BACKGROUND OF THE INVENTION

The present invention relates to a novel technique for producing catalysts especially useful in oxidation and ammoxidation reactions.

Catalysts found especially useful in oxidation and ammoxidation reactions are usually composed of complex compositions of mixed metal oxides. Typically, these materials are made by forming an aqueous solution or slurry of the metals in the catalyst, evaporating the water from the slurry to form a precipitate, and calcining the precipitate in the presence of oxygen at elevated temperatures to form the oxide complex.

In forming such aqueous slurries, it is customary to introduce various catalyst metals in the form of salts which have heat-decomposable anions or cations. For example, molybdenum is frequently introduced into such aqueous compositions in the form of ammonium molybdate, whereas elements such as iron, bismuth, cobalt, nickel and so forth are often times introduced in the form of nitrates. When an aqueous solution or slurry containing such salts is dried, the precipitate obtained contains not only the metals of the objective catalyst but also various heat-decomposable salts such as ammonium nitrate.

In normal catalyst preparations, the pre-catalyst precipitate is heated at an elevated temperature, e.g. 400° C., for a period of about 1 to 4 hours before catalyst calcination. This pre-heating step serves to drive-off substantially all of the heat-decomposable ingredients such as nitrates, which might be present. Thereafter, the pre-heated pre-catalyst is calcined in the presence of oxygen to form a catalytic material of appropriate composition.

Catalytic materials produced in this manner are often times in the form of a very fine powder. Since powdery materials are normally unsuitable for use as fixed-bed catalysts, it is usually necessary to agglomerate the powder into large-sized particles or beads. Normally this is done by tableting, wherein a small amount of binder is mixed with the powder and the mixture so obtained formed into tablets by a suitable machine.

Although fixed-bed catalysts produced by this procedure may exhibit good catalytic properties, it would be beneficial if fixed-bed catalysts made from powders could be produced in such a way so as to have even better catalytic properties.

Accordingly, it is an object of the present invention to provide a novel catalyst preparation technique for forming fixed-bed catalysts with improved catalytic properties.

SUMMARY OF THE INVENTION

This and other objects are accomplished in accordance with the present invention which is based on the discovery that catalysts with improved catalytic properties can be obtained by a novel catalyst preparation technique in which not all of the heat-decomposable salt in the pre-catalyst precipitate is driven off therefrom during the pre-heating phase, if any, and thereafter the powdery catalytic material is agglomerated to larger-sized beads or pellets by dropping a slurry of the powder onto a bed of powder of the same chemical composition.

Thus, the present invention provides a novel process for producing a metal-containing complex oxide catalyst comprising: forming a pre-catalyst containing all of the metals in the catalyst as well as at least one heat-decomposable material, optionally pre-heating the pre-catalyst to remove no more than 90% of the heat-decomposable material therefrom, forming an aqueous slurry of the pre-catalyst, dropping the slurry in the form of droplets onto a particle bed whereby droplets of the slurry agglomerate into essentially spherical agglomerates, and calcining the agglomerates in the presence of oxygen to form the catalyst.

DETAILED DESCRIPTION

The inventive catalyst preparation technique is applicable to the manufacture of any type of oxide complex catalyst whose preparation includes pre-heating and then calcining a pre-catalyst containing a heat-decomposable material. Catalysts of this general type having widely varying compositions are well known in the art. For example, see U.S. Pat. No. 3,642,930, the disclosure of which is incorporated herein by reference.

Pre-catalysts containing at least one heat-decomposable material, usually a salt in addition to the metals to be incorporated into the objective catalysts can be produced by any technique. For example, a heat-decomposable inorganic material, e.g. ammonium nitrate, can be added to the other ingredients of the pre-catalyst during pre-catalyst preparation. Alternately, an organic material which will decompose at the elevated temperatures encountered during catalyst calcination can be added during pre-catalyst preparation.

Normally, however, pre-catalysts containing heat-decomposable material are produced by precipitation from aqueous solutions or slurries of salts of the metals in the catalyst, these salts normally containing heat-decomposable cations and/or anions. Of course, in such preparation not all of the metals must be supplied to the aqueous solution or slurry in the form of salts having a heat-decomposable cations and/or anions. For example, oxides such as molybdenum oxide, cobalt oxide and nickel oxide, acids such as molybdic acid and phosphoric acid, and bases such as potassium hydroxide are often used. Also organic material such as phenyl iron can be used to supply metal components the organic portions of such molecules being heat-decomposable. In any event, all that is necessary is that the pre-catalyst be made in such a way that at least one heat-decomposable material is present.

In the most usual preparation technique, most of the metals of a catalyst are supplied to the aqueous solution or slurry either in the form of nitrates or ammonium salts. Thus, the heat-decomposable material in the pre-catalyst will usually be ammonium nitrate, but could also be only the metal nitrates and/or ammonium salts themselves.

Once the pre-catalyst is formed, it is normally heated to remove a portion of the heat-decomposable material. In accordance with the prior art, pre-heating is accomplished to remove substantially all of the heat-decomposable material (e.g. ammonium nitrate, metal nitrates, unreacted acid, etc.). In accordance with the present invention, pre-heating is accomplished to remove no more than 90%, preferably 50 to 85% of this decompositionable substance. In fact, the pre-heating step can be eliminated altogether.

Determining exactly how to accomplish pre-heating so as to remove the desired amount of heat-decomposable material can be easily accomplished by trial and error using the initial and final weights of the catalyst sample as an indication of how much heat-decomposable material has been removed.

Once the pre-catalyst is pre-heated to remove a portion of the heat-decomposable material therein, the pre-catalyst powder is then formed into beads or pellets of suitable size for fixed-bed catalysts. In accordance with the present invention, this technique is accomplished by forming a slurry, preferably aqueous, of the pre-catalyst powder and then dropping droplets of this slurry onto a bed of powder having the same composition as the pre-catalyst.

Procedures for forming aggregates by dropping slurries onto particle beds are well known. See, for example, U.S. Pat. No. 3,966,639, the disclosure of which is incorporated herein by reference. The same procedure as described in that patent can be used in the inventive process, and it has been found that agglomerates having an essentially spherical shape will be obtained when using this technique.

Once the spherical particles are formed and sufficiently dried, they are removed from the particle bed and heated to remove residual heat-decomposable material. In this regard, it has been found that if the hardened agglomerates produced as described above are subjected to conventional calcination conditions without such a heating operation, they may shatter during calcination. Therefore, the agglomerates are heated under moderate conditions (i.e. above the temperature appropriate for gentle drying but below the temperature at which calcination occurs) to remove residual heat-decomposable material and thereby avoid the shattering problem. Most conveniently, this heating step is accomplished by gradually raising the temperature of the agglomerates from the temperature encountered during the hardening step (e.g. 85° C.) to a temperature approaching calcination temperature (e.g. 425° C.) over a suitable period of time (e.g. 4 hours).

After removal of residual nitrates, the agglomerates are calcined. Calcining is conducted by heating the agglomerates in the presence of molecular oxygen at temperatures of 175° C. to 500° C. preferably 205° C. to 425° C. for 0.2 to 10 preferably 1 to 5 hours preferably in a programmed manner. This is well known by those skilled in the art, the precise calcining conditions vary from catalyst to catalyst depending upon chemical composition and can be determined by routine experimentation.

A significant advantage of the inventive process is that the agglomerates obtained have a relatively high crush strength compared to aggregates in which no decomposable salt remained in the pre-catalyst. Therefore, it is unnecessary to add binder such as silica sol to the aqueous slurry to be dropped. Of course, silica or other binding agents can be added to the slurry if desired to increase particle strength. Also, the addition of binding agents may in some instances contribute to an increase in viscosity and/or surface tension of the aqueous slurry and hence an increase in the size of agglomerates ultimately produced.

Another advantage of the present invention is that there is little or no migration of smaller particles of catalyst to fill-up the pores of the catalyst agglomerate. Therefore, the agglomerates produced by the inventive process have a relatively high degree of porosity. Although not wishing to be bound to any theory, applicants believe that this is one reason why the catalysts produced by the inventive process exhibit good catalytic properties.

As indicated above, significant aspect of the present invention is that the catalyst agglomerates produced have significant porosity. This advantage is believed due to the fact that when the pre-catalyst agglomerates are formed, they exhibit essentially no skin effect. In contrast to the amphora aggregates of previously mentioned U.S. Pat. No. 3,966,639, little or no migration of smaller particles to fill up the pores occurs here. Thus, when the essentially spherical pre-catalysts are agglomerated, they exhibit an excellent degree of porosity.

Another feature of the present invention is that it is possible to control the relative porosity of the catalyst particles produced by changing the amount of heat-decomposable material driven off the pre-catalyst powder during the pre-heating step. If catalysts with high porosity are desired, then less heat-decomposable material is driven off the pre-catalyst during pre-heating so that a larger amount is left for driving off during calcination. If less porosity is desired then more heat-decomposable salt is driven off during pre-heating.

The catalyst agglomerates produced by the inventive process are ideally suited for use as fixed-bed catalysts for a wide variety of different reactions such as oxidation of olefins, ammoxidation of olefins, oxydehydrogenation reactions and the like. The spherical shape of the catalysts provides the advantages of good packing efficiency, good pressure drop characteristics, high strength, non-dusting, and absence of skin effects. Higher defusion, higher reactivity and lower operating temperatures are possible advantages of these catalysts.

In order to more thoroughly describe the inventive process, the following experiments were conducted:

EXAMPLE 1

87.3% $K_{0.1}Co_{4.5}Ni_{2.5}Fe_{3.0}Bi_{1.0}P_{0.5}Mo_{12}O_{50.3}$ -12.7% $SiO_2$ 4,761 grams of ammonium heptamolybdate and 6,361 grams of water was admixed with 28.0 grams of a 45% aqueous potassium hydroxide solution. Approximately 450 grams of Degussa Aerosil was added to the resultant solution. 9,220.5 grams of a metal nitrate solution comprising 91% metal nitrate-9% water, and 129.6 grams of an 85% aqueous reagent grade $H_3PO_4$ solution were then added. The resultant slurry became very viscous and 1,000 cc additional $H_2O$ was added along with another 450 grams Degussa Aerosil, the total amount of silica added being 904 grams. After stirring approximately one hour, the slurry was mixed in a Waring blender and an additional 200 cc of water added. The viscosity of the slurry was approximately 1,400 cps. The slurry was then spray dried to form a pre-catalyst containing ammonium nitrate as a heat-decomposable salt.

The pre-catalyst was then processed to remove approximately 80% of the residual ammonium nitrate. This was accomplished by heating the pre-catalyst in a furnace in the presence of oxygen at 250° C. until the weight reduction of the pre-catalyst was approximately 28%.

After the pre-heating operation, the pre-catalyst was slightly tumbled to break-up all of the lumps therein and then passed through a 10 mesh screen. The pre-catalyst powder so obtained was then formed into agglomerates in the following series of runs.

Run 1A 210.7 grams of the above pre-catalyst and 11.6 grams of Degussa Aerosil 200 were mixed together with 67 cc of water in an Osterizer blender. 5 cc of water was added to the mixture so that it could be poured out of the blender. The gel so obtained was allowed to set overnight.

The next morning, the gel was very thick and therefore an additional 10 cc of water was added and the slurry reblended for 60 seconds. A portion of the slurry was then filled into an eyedropper and dropped into a pan containing a powder of the same composition as the pre-catalyst, the powder having a mixture of particle sizes in the range of 5-100 microns. The individual droplets falling from the dropper when reaching the particle bed agglomerated into essentially spherical agglomerates and then hardened as they were gently heated. Residual nitrate in the agglomerates was then removed by heating the agglomerates for four hours at a periodically increasing temperature beginning with 85° C. and ending with 425° C. The catalyst agglomerates were then calcined for five hours at 550° C. in the presence of air. The surface area of the catalyst so obtained was measured to be 19.1 m$^2$/gm.

Run 1B

Essentially the same procedure as in Run 1A was accomplished except that 29 grams of the 40% silica gel (Nalco 41001) was employed in place of the 11.6 grams of Aerosil 200. The aqueous slurry obtained after standing was very fluid in nature. The agglomerated pre-catalyst was roughly spherical, and the pre-catalyst was denitrified as in Run 1A and calcined for 3 hours at 570° C. rather than 5 hours at 550° C. to form the active catalyst. The surface area of the catalyst obtained was 15.7 m$^2$/gm.

EXAMPLE 2

Pre-Catalyst Preparation

An ammoxidation catalyst having the formula 82.5%-Co$_{4.5}$Ni$_{2.5}$Fe$_3$K$_{0.07}$Bi P$_{0.5}$Mo$_{12}$O$_{50.3}$-17.5% SiO$_2$ was prepared as follows:

4,016 grams of ammonium heptamolybdate, (NH$_4$)$_6$Mo$_7$O$_{24}$·4H$_2$O, were added to 8,907 grams of water with stirring. To this solution were added 109 grams of phosphoric acid and 555 grams of Aerosil silica sol, and the resulting slurry was stirred until the contents were well dispersed. To this slurry the following solutions were added in the sequence given:

2,482.5 grams of Co(NO$_3$)$_2$·6H$_2$O and 1,378 grams of Ni(NO$_3$)$_3$·6H$_2$O dissolved in 6,325 grams of water at 50-60 degrees C.;

2,297 grams of Fe(NO$_3$)$_3$·9H$_2$O dissolved in 422 grams of water at 50-60 degrees C.;

919.5 grams of Bi(NO$_3$)$_3$·5H$_2$O dissolved in a mixture of 717 grams of water and 91.2 grams of nitric acid at 60-75 degrees C.;

171 grams of KNO$_3$ dissolved in 40 cc of warm water. An additional 555 grams of Aerosil silica sol was then added and the entire mixture was stirred for an additional 30-45 minutes.

The catalyst slurry was spray dried and partially denitrified by a programmed heat treatment to remove 70-75% of the removable nitrates.

Agglomerate Preparation

To 105 grams of water were added 200 grams of the above partially denitrified catalyst powder. After thorough mixing, the slurry was blended in an Osterizer blender for 3 minutes. The slurry was then dropped onto a bed of calcined powder of the same composition as the final spherical catalyst, and heated gently under a heat lamp to dry the spheres. The almost spherical catalyst was then heat treated to remove the remaining nitrates and then calcined for 5 hours at 550° C. The generally spherical catalyst had diameters of 3.1 mm.

COMPARATIVE EXAMPLE

In order to demonstrate the advantages of the inventive process, catalysts of the same composition as that prepared in Example 2 were produced by a technique outside the scope of the invention. In this preparation, a portion of the partially denitrified pre-catalyst powder produced in Example 2 was formed into tablets by conventional techniques. In accordance with this preparation, 1% graphite was added to the partially denitrifed catalyst powder and the mixture so obtained was then tableted, the tablets obtained had dimensions of 5 mm×2.8 mm and were further heat treated to remove the remaining nitrates and then were calcined at 550° C. for 5 hours.

In order to determine the relative properties of these different catalysts, they were employed in the conversion of propylene to acrylonitrile. In this comparison, feed comprising 1 propylene/1.2 NH$_3$/10air/3 H$_2$O was fed to a fixed-bed reactor packed with each of the above catalysts. The contact time was 2.5 seconds and the reaction temperature was varied. The results obtained are set forth in the following Table I.

TABLE I

Comparison of Spherical Catalyst and Tableted Form of Ammoxidaion Catalyst for the Conversion of Propylene to Acrylonitrile

| Example | Catalyst Form | Reaction Temp. °C. | % Per Pass Conv to AN | Useful Yield | Selectivity to AN |
|---|---|---|---|---|---|
| Comp A | Tablet | 400 | 74.7 | 93.6 | 82.9 |
| 1 | Spherical | 400 | 82.1 | 96.0 | 87.3 |
| Comp B | Tablet | 415 | 83.8 | 94.7 | 87.1 |
| 2 | Spherical | 415 | 85.4 | 96.7 | 90.2 |
| Comp C | Tablet | 425 | 86.2 | 94.8 | 87.2 |
| 3 | Spherical | 425 | 87.6 | 96.3 | 89.7 |

From the foregoing, it can be seen that acrylonitrile is obtained in every instance in higher yields when spherical catalysts of the present invention are employed. Thus it is clear that the present invention provides a novel improvement over known catalysts preparation techniques.

Although only a few embodiments of the present invention have been specifically described above, it should be appreciated that many modifications can be made without departing from the spirit and scope of the invention. For example, the chemical composition of the powder bed can be different from that of the catalyst to be produced rather than the same as taught in U.S. Pat. No. 3,966,639. All such modifications are intended to be included within the scope of the present invention, which is to be limited only by the following claims.

We claim:

1. A process for producing a metal-containing complex oxide catalyst comprising:
   forming a pre-catalyst containing all of the metals in said catalyst as well as at least one heat-decomposable material,
   forming an aqueous slurry from said pre-catalyst, dropping said slurry in the form of droplets onto a particle bed whereby droplets of said slurry agglomerate into essentially spherical agglomerates, and calcining said agglomerates in the presence of oxygen to form said metal-containing complex oxide catalyst, no more than 90% of said heat-decomposable material being removed from said pre-catalyst prior to forming said slurry.

2. The process of claim 1 wherein the particles of said particle bed have a composition essentially the same as the composition of said pre-catalyst or said complex oxide catalyst.

3. The process of claim 1 wherein said pre-catalyst is pre-heated so as to drive off 50 to 85% of said heat-decomposable material prior to forming said slurry.

4. The process of claim 3 wherein said heat-decomposable material is ammonium nitrate.

5. The process of claim 1 wherein said agglomerates are heated after forming on said particle bed and prior to being calcined in order to drive off residual heat-decomposable material.

6. The process of claim 5 wherein said pre-catalyst is pre-heated so as to drive off 50 to 85% heat-decomposable material prior to forming said slurry.

7. The process of claim 6 wherein said heat-decomposable material is ammonium nitrate.

8. The process of claim 1 wherein said pre-catalyst further contains a binder.

9. The process of claim 8 wherein said binder is silica.

10. The process of claim 1 wherein a binder is mixed with said aqueous slurry prior to dropping of said aqueous slurry onto said particle bed.

11. The process of claim 10 wherein said binder is silica.

* * * * *